United States Patent
Baker et al.

(10) Patent No.: US 8,524,963 B2
(45) Date of Patent: Sep. 3, 2013

(54) SUPPORTED ORGANOIRIDIUM CATALYSTS FOR ALKANE DEHYDROGENATION

(75) Inventors: R. Thomas Baker, Los Alamos, NM (US); Alfred P. Sattelberger, Darrien, IL (US); Hongbo Li, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 1022 days.

(21) Appl. No.: 12/079,477

(22) Filed: Mar. 27, 2008

(65) Prior Publication Data

US 2008/0249343 A1    Oct. 9, 2008

Related U.S. Application Data

(60) Provisional application No. 60/920,489, filed on Mar. 27, 2007.

(51) Int. Cl.
C07C 5/333 (2006.01)
C07C 5/52 (2006.01)
B01J 31/12 (2006.01)

(52) U.S. Cl.
USPC ........... 585/433; 502/152; 502/154; 585/656; 585/660

(58) Field of Classification Search
None
See application file for complete search history.

(56) References Cited

PUBLICATIONS

John et al, Organometallics, 2001, 20, 296-304.*
Silvennoinen et al. Applied surface science 253 (2007), 4103-4111.*
Basset et al., Coord. Chem. Rev., 1998, 178-180, 1703.*
Li et al. Abstracts of pagers, 233rd ACS National Meeting, Chicago, IL, United States, Mar. 25-29, 2007, pp. INOR-645.*
Loften et al. Applied catalysis A: General 299, 250-257, 2006.*
Ward et al., JCS, Chem. Comm., 1980, 357.*

* cited by examiner

*Primary Examiner* — Yun Qian
(74) *Attorney, Agent, or Firm* — Bruce H. Cottrell; Samuel L. Borkowsky

(57) ABSTRACT

Solid supported organoiridium catalysts, a process for preparing such solid supported organoiridium catalysts, and the use of such solid supported organoiridium catalysts in dehydrogenation reactions of alkanes is provided. The catalysts can be easily recovered and recycled.

4 Claims, 1 Drawing Sheet

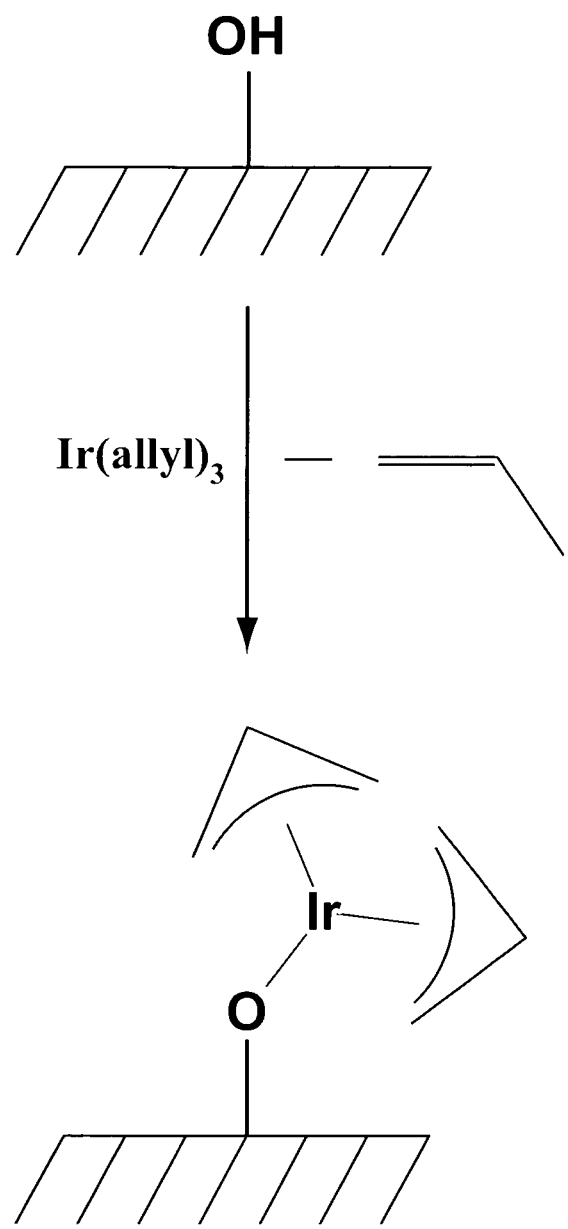

SUPPORTED ORGANOIRIDIUM CATALYSTS FOR ALKANE DEHYDROGENATION

RELATED APPLICATIONS

This application claims the benefit of Provisional Application Ser. No. 60/920,489 filed Mar. 27, 2007.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to supported organoiridium catalysts, to the preparation of such supported catalysts and their use in catalysis reactions.

BACKGROUND OF THE INVENTION

Most useful alkane conversion processes (such as dehydrogenation and dehydrocoupling) are endothermic and generate hydrogen. Typical heterogeneous catalysts require high temperatures and usually exhibit low selectivities. Trivalent iridium complexes of tridentate bis(phosphine) ligands (i.e., 'pincer' ligands) have shown unprecedented activity for selective alkane dehydrogenation catalysis. Such homogeneous catalysts operate at lower reaction temperatures and are typically run in open systems to drive the reaction by allowing release of hydrogen. Alternatively, use of a bulky alkene acceptor, such as t-butylethylene, can also be used to absorb the hydrogen product and help drive the alkane dehydrogenation reaction. These catalysts have also recently attracted a great deal of attention from their use in a tandem alkane dehydrogenation/metathesis scheme for upgrading low carbon number refinery waste streams to higher carbon number fuels. However, these catalysts suffer from: 1) bimolecular decomposition reactions under operation conditions; 2) product inhibition—high alkene concentrations prevent binding of alkane substrates; 3) isomerization of targeted terminal alkene products to less valuable internal alkenes; and, 4) difficulties with catalyst separation and recycle. Immobilization of organometallic moieties on active surfaces can, in principle, circumvent all the problems noted above and will also allow dehydrogenation of gaseous substrates such as ethane and propane.

Previous examples of immobilization included reactions of $Rh(allyl)_3$ with silica. Metal allyl complexes are potentially excellent to form a family of supported catalysts, since the allyl ligand can easily go through p-s conversion, thus allowing a variety of other electron donating ligands bonded to the metal. The resulting $Rh(allyl)_2(O—)$ species and related moieties were characterized in detail and shown to be active for alkene hydrogenation catalysis. The stability of these rhodium catalysts however was limited by reduction at the metal center (to rhodium metal) and organic fragment transfer to the surface (i.e., to afford allyl-O—Si species). Corresponding studies of the potentially more stable iridium analog were hampered by lack of an efficient route to $Ir(allyl)_3$.

The high-yield preparation of $Ir(allyl)_3$ was previously shown (John et al., Organometallics 2001, 20, 296) wherein a rich ligand substitution chemistry was also demonstrated to provide $Ir(allyl)_3(L)_n$ without reduction of the trivalent iridium center even with a strong acid ligand of carbon monoxide. Unfortunately, the $Ir(allyl)_3$ and its derivatives were found unreactive with active silica surfaces or substrates.

SUMMARY OF THE INVENTION

In accordance with the purposes of the present invention, as embodied and broadly described herein, the present invention includes a catalytic material comprising a reaction product of organoiridium tri-allyl and a solid support characterized by a Hammett acidity greater than that of silica, said iridium characterized as trivalent.

In one embodiment, the organoiridium tri-allyl further includes a phosphine substituent.

The present invention further provides a process for catalytic dehydrogenation of a dehydrogenable hydrocarbon comprising contacting the dehydrogenable hydrocarbon with the catalytic material comprising a reaction product of organoiridium tri-allyl and a solid support characterized by a Hammett acidity greater than that of silica.

BRIEF DESCRIPTION OF THE DRAWINGS

FIG. 1 shows a schematic drawing of the process for preparing the catalytic material of the present invention through reaction of an organoiridium triallyl compound ($Ir(allyl)_3$) with a solid support of sulfated zirconia or de-hydroxylated alumina with the elimination of an allyl group, i.e., a propene or proplyene.

DETAILED DESCRIPTION

The present invention concerns supported organometallic catalysts and especially supported organoiridium catalysts, as well as catalysis processes using such supported catalysts.

The present invention provides benefits over prior homogeneous catalysts. Such benefits include: the elimination of bimolecular decomposition pathways, i.e., as the catalyst material is fixed upon a support, it cannot interact with itself; greater thermal stability; and, facile recovery and recycle of the catalyst from the reaction products. When the catalysis is conducted in a flow reactor, the catalysts of the present invention also offer the potential for minimization of product inhibition and isomerization, and the potential for use with typically gaseous alkane substrates, such as ethane, propane, butane and the like. Thus, the catalysts of the present invention can potentially be valuable for a variety of tandem catalysis schemes derived from inexpensive feedstocks such as propane.

In the present invention, the solid support can generally be active surfaces having a Hammett acidity value ($H_o$) greater than that of silica. Such a Hammett acidity value is generally lower than about −5. Such solid supports can be, e.g., alumina ($H_o$ from about −5 to about −10) and sulfated zirconia ($H_o$ of about −16) or may be any suitable zeolite material having the required Hammett acidity value.

Reaction of $Ir(allyl)_3$ or its derivatives with a solid support material such as alumina or sulfated zirconia can yield a composite catalytic material of a supported $Ir(allyl)_2(O—)$ species and release propene (from the displaced allyl group). Similar reactions have been observed for ligated derivatives such as $Ir(allyl)_3(L)_n$ where L is a phosphine such as triphenyl phosphine, methyl diphenyl phosphine, dimethylphenyl phosphine or a bridged di-phosphine such as 1,2-$(PPh_2)_2$-$C_6H_4$ and n is 1 or 2. Generally, phosphine-ligated catalysts have shown better thermal stability allowing for reaction temperatures up to about 330° C. whereas the catalysts without the phosphine addition generally allow reaction temperatures of only up to about 270° C. to about 280° C. In addition, phosphine-ligated catalysts have shown somewhat longer lifetimes. The resulting immobilized catalysts have been employed in a variety of alkane dehydrogenation reactions and have been found to be easily recycled after the reaction.

The present invention provides solid supports that efficiently anchor trivalent organoiridium moieties. Such anchored or solid supported trivalent organoiridium moieties can be used for selective alkane dehydrogenation.

Suitable alkane substrates for dehydrogenation can generally include cyclic alkanes such as cyclohexane, methylcyclohexane, ethylcyclohexane, cyclooctane, cyclodecane and the like, and acyclic alkanes, generally including from about 2 to 12 carbon atoms, such as ethane, propane, butane, pentane, hexane, heptane, octane, nonane and the like. The alkanes may be straight chain alkanes or may be branched. Where an acyclic alkane is used as a starting feedstock, the dehydrogenation reaction can generally include a hydrogen acceptor, although a hydrogen acceptor may not always be required.

Suitable hydrogen acceptors can include an olefin such as tert-butylethylene, norbornylene and the like.

Typical reaction parameters for the dehydrogenation, such as catalyst loading, temperature, and reaction time, can be generally varied and will be interrelated such that higher catalyst loadings can reduce reaction time. Generally, the reaction temperature will be from about 200° C. up to a temperature below the decomposition temperature of the catalytic material. For the non-phosphine ligated moiety the temperature can generally be from about 200° C. to about 280° C. whereas for the phosphine ligated allyliridium moieties the temperature can generally be from about 200° C. to about 330° C.

The present invention is more particularly described in the following example that is intended as illustrative only, since numerous modifications and variations will be apparent to those skilled in the art.

EXAMPLE A

An active support was synthesized as follows. A support of sulfated zirconia was prepared by thermal decomposition of $Zr(SO_4)_2 \cdot 4H_2O$ (3.5 g, Aldrich, 99%) at about 730° C. for 5 hour (hr) in flowing air (100 milliliters per minute (mL/min)). Then the samples were activated in flowing Ar (100 mL/min) for about 45 minutes and subsequently under vacuum for about 75 minutes at 400° C.

Alumina (2.5 g) was placed in a reactor, a flow of helium was established through it and the alumina was activated with helium, at 1000° C. for a period of 0.3 hr to give dehydroxylated alumina.

EXAMPLE 1

The precursors of $Ir(allyl)_3$ and $Ir(allyl)_3(PPh_3)$ were prepared in accordance with the description of John et al., Organometallics 2001, 20, 296, such description incorporated herein by reference.

Immobilization of iridium complexes on the support was accomplished as follows. Supported organoiridium catalysts were prepared by exposing the acidic support (500 mg) to 10 mg of the iridium complex of interest in pentane solution at room temperature for about 1 hour (h). The resulting catalyst was then collected by filtration and washed with pentane at room temperature to remove any physisorbed metal hydrocarbyl. The quantity of metal hydrocarbyl present on the support after the chemisorption process was determined by digesting samples using aqueous HF solution and then measuring Ir content by inductively-coupled plasma (ICP) spectroscopy. The iridium loading was determined to be 0.3% for sulfated zirconia as the support and 1.1% for dehydroxylated alumina as the support. The supported catalysts were also characterized by infrared and solid state MASNMR spectroscopy.

After chemisorbing the complexes $Ir(allyl)_3$ on sulfated zirconia or dehydroxylated alumina in pentane slurry reactions, only propylene (0.8 propylene per iridium) was detected by in situ $^1H$ NMR spectroscopy, indicating that the Brønsted acid sites effected protonolysis of one Ir-allyl group to give the supported $Ir(allyl)_2O$-moiety.

EXAMPLE 2

Catalytic alkane dehydrogenation reactions were performed as follows. Acceptorless Cycloalkane Dehydrogenation reaction: To a 50 mg dehydroxylated alumina supported $Ir(allyl)_2O$-catalyst was added 0.1 mL of cyclohexane in a Schlenk tube in the glove box. The tube was cooled to −78° C., evacuated, and sealed. The tube was then heated at from about 200 to about 280° C. for about 15 hours. The dehydrogenated products were then characterized by GC-MS and NMR spectroscopy to give 95% conversion to benzene from the cyclohexane. After transferring the product, the catalyst was easily recovered or reused for an additional two cycles with essentially unchanged activities.

Acyclic-alkane dehydrogenation reactions with a hydrogen acceptor: To a 50 mg dehydroxylated alumina supported $Ir(allyl)_2O$-catalyst was added to 0.1 mL of heptane and 0.1 mL of tert-butylethylene as a hydrogen acceptor in a Schlenk tube in the glove box. The tube was cooled to −78° C., evacuated, and sealed. The tube was then heated at about 200 to about 280° C. for about 15 hours. The dehydrogenated products of 1-heptene, cis- and trans-2-heptenes were then measured by GC-MS and NMR spectroscopy to give a heptane conversion of 15%.

EXAMPLE 3

Other cyclic alkane substrates of methylcyclohexane and ethylcyclohexane were dehydrogenated using similar procedures and conditions. It was found that the conversion of methylcyclohexane to toluene was about 50% under similar conditions for which cyclohexane conversion to benzene was complete. Ethylcyclohexane to ethylbenzene conversion was 33% under these conditions. Upon examining additional cycloalkanes under the same reaction conditions, cyclooctane was dehydrogenated in 80% conversion to a 1.3:1 ratio of ethyl benzene and dimethylbenzene (Claisen rearrangement) whereas conversion of cyclodecane was 77% to a 1:1 ratio of naphthalene and diethyl benzene.

What is claimed is:

1. A catalytic material capable of catalyzing a dehydrogenation of alkanes to form alkenes, said catalytic material comprising a reaction product of a slurry based reaction of a trivalent triallyliridium compound and a solid support of dehydroxylated alumina or sulfated zirconia, said reaction product characterized as having trivalent diallyliridium moieties that are bonded from iridium atoms of the diallyliridium moieties to oxygen atoms of said support.

2. The catalytic material of claim 1 wherein said triallyliridium compound further includes a phosphine ligand.

3. The catalytic material of claim 2 wherein said phosphine ligand is triphenyl phosphine.

4. The catalytic material of claim 1 wherein said solid support is sulfated zirconia.

* * * * *